United States Patent [19]

Raju et al.

[11] Patent Number: 5,468,865
[45] Date of Patent: Nov. 21, 1995

[54] STEREOPREFERENTIAL SYNTHESIS OF 3-(1-PHENYLPROP-2-YL)-5-PHENYLOXAZOLIDINONES

[75] Inventors: Muppala S. Raju; Vikram Khetani, both of Bridgewater, N.J.

[73] Assignee: Celgene Corporation, Warren, N.J.

[21] Appl. No.: 237,190

[22] Filed: May 3, 1994

[51] Int. Cl.$^6$ ............................................. C07D 263/20
[52] U.S. Cl. .................................................... 548/229
[58] Field of Search ................................... 548/299, 230, 548/231, 232

[56] References Cited

U.S. PATENT DOCUMENTS

| | | | |
|---|---|---|---|
| 4,619,919 | 10/1986 | Gold et al. | 514/166 |
| 4,658,060 | 4/1987 | Gold et al. | 564/304 |
| 4,879,233 | 11/1989 | Charney | 435/254 |
| 5,245,053 | 9/1993 | Bloom et al. | 549/435 |

FOREIGN PATENT DOCUMENTS

| | | | |
|---|---|---|---|
| 399070 | 4/1991 | Japan | 548/229 |

OTHER PUBLICATIONS

Bloom et al., "Disodium (R,R)-5-[2-[[2-(3-Chlorophenyl)-2-hydroxyethyl]-amino]propyl]-1,3-benzodioxole-2,2-dicarboxylate (CL 316,243). A Potent β–Adrenergic Agonist Virtually Specific for β$_3$ Receptors. A Promising Antidiabetic and Antiobesity Agent", *J. Med. Chem.*, 35, pp. 3081–3084 (1992).

Itoh et al., "Friedel–Crafts α–Aminoacylation of Alkylbenzene with a Chiral N–Carboxy–α–amino Acid Anhydride without Loss of Chirality", *J. Org. Chem.*, 57, pp. 7334–7338 (1992).

Kashima et al., "Synthesis and Stereoselective Reactions of 2-(Pyrrol-1-yl)alkanals and 2-(Pyrrol-1-yl)alkan-1-ones", *J. Chem. Soc. Perkin Trans. 1*, pp. 1041–1046 (1989).

Maibaum et al., "A Facile Synthesis of Statine and Analogues by Reduction of β–Keto Esters Derived from Boc–Protected Amino Acids. HPLC Analyses of Their Enantiomeric Purity", *J. Org. Chem.*, 53, pp. 869–873 (1988).

Ookawa et al., "Asymmetric Synthesis of Optically Active threo– and erythro–Pyrrolidinylbenzyl Alcohol by the Highly Stereospecific arylation of (S)–Proline and the Subsequent Highly Diastereoselective Reduction of the α–Amino Ketone", *J. Chem. Soc. Perkin Trans. 1*, pp. 1465–1471 (1987).

Raddatz et al., "Reduction with Yeast Cells, the Key Step of an Efficient Synthesis of (3S, 4S)–4–Amino–3–hydroxypentanoic Acids", *Angew. Chem. Int. Ed. Engl.*, 27:3, pp. 426–427 (1988).

Reetz et al., "Non-Racemizing Synthesis and Stereoselective Reduction of Chiral α–Amino Ketones", *Tetrahedron: Asymmetry*, 1:6, pp. 375–378 (1990).

Soai et al., "Highly Stereospecific Arylation of (S)–Proline and Complementary Highly Diastereoselective Reduction of the α–Amino Ketone. Asymmetric Synthesis of (1S, 2'S)–and (1R, 2'S)–Phenyl(2'–pyrrolidinyl)methanol", *J. Chem. Soc., Chem. Commun.*, pp. 412–413 (1986).

Wanner et al., "Chelat–Und Nicht–Chelat–Kontrollierte Reduktionen Von β–Amido–Ketonen: Synthese Nicht–Racemischer 1,3–Aminoalkohole Mit Pyrrolidinstruktur", *Tetrahedron*, 47:10/11, pp. 1895–1910 (1991).

*Primary Examiner*—Donald G. Daus
*Attorney, Agent, or Firm*—Mathews, Woodbridge & Collins

[57] ABSTRACT

The (R,R)-diastereoisomer of oxazolidin-2-ones, which are chemical intermediates for the preparation therapeutic agents useful in the treatment of diabetes and hyperglycemia, are prepared substantially free of isomeric forms through reduction of an acid addition salt of an (R)-N-protected-N-phenylcarboxymethyl-1-phenylprop-2-ylamine to form a secondary alcohol of predominantly the (R,R) chiral form in preference to others, removal of the protecting group to form a secondary amine, and allowing the secondary amine to react with a source of carbonyl groups. A typical embodiment involves the preparation of (R,R)-3-[1-(3,4-dimethoxyphenyl)prop-2-yl]-5-(3-chlorophenyl)oxazolidin-2-one in which both the chemical purity and optical purity are in excess of 99%.

21 Claims, No Drawings

STEREOPREFERENTIAL SYNTHESIS OF 3-(1-PHENYLPROP-2-YL)-5-PHENYLOXAZOLIDINONES

BACKGROUND OF THE INVENTION

U.S. Pat. No. 5,245,053, the disclosure of which is incorporated herein by reference, describes a series of 1,3-benzodioxoles useful in the treatment of diabetes and hyperglycemia, of which (R,R)-(−/−)-5-[2-{2-(3-chlorophenyl)-2-hydroxyethyl}aminopropyl]-1,3-benzodioxole-2,2-dicarboxylic acid, its esters, and salts are representative.

Other pharmacological agents described in the literature also contain the N-(2-phenyl-2-hydroxyethyl)-2-aminopropylphenyl structure, as for example, 2-[2-(3-chlorophenyl)-2-hydroxyethyl] -1-(4-carbomethoxyphenyl)-2-[ 2-(3-chlorophenyl)-2-hydroxyethyl]aminopropane {BRL 26830}; 1-(4-methoxycarbonylmethoxyphenyl)-2 -[2-(3-chlorophenyl)-2-hydroxyethyl]aminopropane {BRL 35135}; and N,N-bis-{2-[2-(3-chlorophenyl)-2-hydroxyethyl]} -1-(4-[2-ethoxyethoxy]phenyl)-aminopropane {Ro 40-2148}.

These compounds, which possess at least two centers of chirality, can be prepared through a variety of multistep syntheses. In one embodiment for the preparation of (R,R)-(−/−)-5-[2-{2-(3-chlorophenyl)-2-hydroxyethyl} aminopropyl]-1,3-benzodioxole-2,2-dicarboxylic acid characterized in U.S. Pat. No. 5,245,053 as preferred, the synthesis begins with the reductive amination of a 3,4-dimethoxyphenylacetone to with 2-phenyl-2-hydroxyethylamine to afford an N-(2-phenyl-2-hydroxyethyl)-1-(3,4-dimethoxyphenyl)prop-2-ylamine. This initial intermediate, which already possesses the two chiral centers of the final product, is treated with carbonyl diimidazole to afford isomeric 3-[1-(3,4-dimethoxyphenyl)prop-2-yl]-5-phenyloxazolidin-2-ones which then are separated by derivatization, chromatography, and regeneration to isolate the desired (R,R)-diastereoisomer. Only the thusisolated (R,R)-diastereoisomer is subjected to the subsequent synthetic steps to produce the final compounds, unwanted isomeric material presumably being discarded.

DETAILED DESCRIPTION

The present invention pertains to a process for the stereopreferential preparation of intermediates yielding compounds with the N-(2-phenyl-2-hydroxyethyl)-2-aminopropylphenyl structure; i.e., one diastereoisomeric form substantially free of isomeric forms. For conciseness' sake, it is exemplified herein with respect the preparation of (R,R)-3-[1-(mono and disubstituted phenyl)prop-2-yl]-5-phenyloxazolidin-2-ones which are known intermediates in the synthesis of (R,R)-(−/−)-5-[2-{2-(3-chlorophenyl)-2-hydroxyethyl}aminopropyl]-1,3-benzodioxole-2,2-dicarboxylic acid.

In particular, the present invention involves a process for the preparation of an (R,R)-oxazolidin-2-one diastereoisomer of the formula:

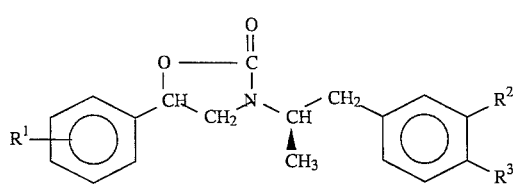

in which

R$^1$ is hydrogen, halogeno, lower alkyl, lower alkoxy or trifluoromethyl;

R$^2$ is hydrogen, lower alkyl, or a phenolic protecting group; and

R$^3$ is hydrogen, lower alkyl, carbo(lower alkoxy), lower alkoxy, or a phenolic protecting group.

In the first step of the process, an acid addition salt of a ketone of the formula:

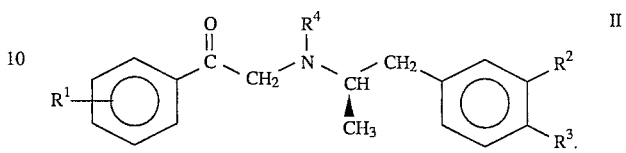

in which each of R$^1$, R$^2$, and R$^3$ is as previously defined and R$^4$ is an aryl(lower alkyl) amino protecting group, is reduced in solution to form a secondary alcohol of the formula:

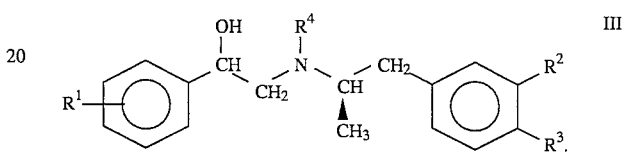

Under these conditions, the secondary alcohol of Formula III is produced predominantly in one chiral form in preference to other forms.

The term "diastereoisomeric enrichment" as used herein refers to the increase in the amount of one diastereoisomer as compared to another. A convenient method of expressing the diastereoisomeric enrichment is the concept of diastereoisomer excess, or "de" expressed by the expression:

$$de = \frac{D^1 - D^2}{D^1 + D^2} \times 100$$

in which D$^1$ is the amount of a first diastereoisomer and D$^2$ is the amount of the second diastereoisomer. Thus if the initial ratio of the two diastereoisomer is 50:50 and an diastereoisomeric enrichment sufficient to produce a final ratio of 50:30 is achieved, the de is 25% whereas if the final ratio is 70:30, the de with respect to the first chiral form is 40%. Typically with the process of the present invention, de's of 90% or greater can be achieved.

The reduction can employ any method which reduces ketones to alcohols, such as catalytic hydrogenation, or chemical reduction with, for example, a borohydride such as potassium borohydride, sodium borohydride, lithium borohydride, lithium(tributoxy)aluminum hydride, sodium boro(acetoxy) hydride, zinc borohydride, and the like. Because of its availability and relatively low cost, sodium borohydride is preferred. Typically a solvent such as methanol, ethanol, isopropanol, diethyl ether, tetrahydrofuran, dioxane, or the like is employed. Generally the reduction is conducted at about 25° C. or below. Preferably it is conducted significantly below about 0° C., e.g. −70° to −78° C., since this has been found to increase stereoselectivity.

The acid addition salts of a compound of Formula II include those derived from organic and inorganic acids such as, without limitation, hydrochloric acid, hydrobromic acid, phosphoric acid, sulfuric acid, methanesulphonic acid, acetic acid, trifluoroacetic acid, tartaric acid, lactic acid, succinic acid, citric acid, malic acid, maleic acid, sorbic acid, aconitic acid, salicylic acid, phthalic acid, embonic acid, enanthic acid, and the like.

The amino protecting group R$^4$ is not found in the final compounds, being removed in the next step of the synthesis.

Since compounds bearing such protecting groups thus are of importance solely as chemical intermediates, the precise structure of the protecting group is not critical to either the reaction or the eventual pharmacological activity. Nevertheless selection of the protecting group $R^4$ advantageously can improve stereoselectivity in the production of the secondary alcohol of Formula III.

Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schröder and Lubke, Academic Press, London and New York, 1965; "Methoden der organischen Chemie", Houben-Weyl, 4th Edition, Vol 15/I, Georg Thieme Verlag, Stuttgart 1974, the disclosures of which are incorporated herein by reference.

The amino group preferably is protected with an aryl-(lower alkyl) group, particularly one which is substituted in the α-position; i.e., benzyl and substituted benzyl, especially substituted benzyl such as 2-methoxybenzyl, 3-methoxybenzyl, 4-methoxybenzyl, 3,4-dimethoxybenzyl, 3,4-diethoxybenzyl, 3-methoxy-4-n-butoxybenzyl, 3-methoxy-4-n-heptoxybenzyl, 3-methoxy-4-benzyloxybenzyl, 3,4-dichlorobenzyl, 3,4-methylenedioxybenzyl, 3,4,5-trimethoxybenzyl, or β-naphthylmethyl, and the like.

The nature of $R^1$ is not critical since this group does not enter into any of the reactions. By reason of the highly desirable biological properties in the ultimate compound, chloro is preferred, particularly in the meta (or 3-) position of the depicted phenyl ring.

The structure of $R^2$ and $R^3$ also is not critical since these groups generally are modified at a later stage and thus can be selected on the basis of economics and convenience. For example, in the synthesis of (R,R)-(–/–)-5-[2-{2-(3-chlorophenyl)-2-hydroxyethyl}aminopropyl] -1,3-benzodioxole-2,2-dicarboxylic acid, $R^2$ and $R^3$ initially each can be lower alkoxy of 1 to 6 carbon atoms, particularly methoxy, or together lower alkylidenedioxy of 1 to 6 carbon atoms, particularly methylenedioxy or isopropylidenedioxy, but these groups are cleaved in the course of forming the benzodioxole ring system.

As used herein, the term lower alkyl denotes a univalent saturated branched or straight hydrocarbon chain containing from 1 to 6 carbon atoms. Representative of such lower alkyl groups are methyl, ethyl, propyl, isopropyl, butyl, isobutyl, sec-butyl, tert-butyl, pentyl, isopentyl, neopentyl, tert-pentyl, hexyl, and isohexyl. Other groups so qualified, such as "lower alkoxy" and "lower alkylidene", are named in accordance with the IUPAC nomenclature conventions as derivatives of lower alkyl.

In the second step of the process, the amino protecting group is removed from the compound of Formula III to form a secondary amine of the formula:

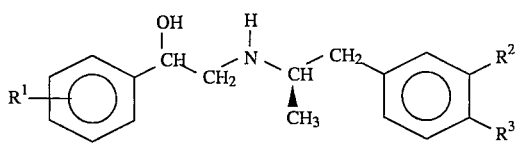

wherein each of $R^1$, $R^2$, and $R^3$ is as defined above.

The conditions employed are those appropriate for the specific amino protecting group. In the case of benzyl or substituted benzyl, for example, the protecting group can be removed through catalytic hydrogenation.

In the final synthetic step of the present process, the secondary amine or a reactive intermediate thereof is allowed to react with a source of carbonyl groups, i.e., compound capable of introducing a carbonyl group to form a carbamate, to form the (R,R)-oxazolidin-2-one of Formula I. Such source of carbonyl groups are essentially activated derivative of carbonic acid, as for example phosgene, carbonyl diimidazole, carbodiimides, and the like.

The third step can be performed without isolation of the secondary amine formed in the second step. Preferably, however, the secondary amine is purified. Moreover, since the immediately following steps in the synthesis of the 1,3-benzodioxoles of U.S. Pat. No. 5,245,053 involve removal of the phenolic protecting groups and formation of the benzodioxole ring system, the (R,R)-oxazolidin-2-one of Formula I in the third step of the present process can be introduced to the sequence of these subsequent steps without isolation. Preferably, however, the (R,R)-oxazolidin-2-one of Formula I formed in the third step is isolated and purified through the use of conventional techniques such as concentration, crystallization, or chromatography.

In a further modification, the secondary alcohol of Formula III is directly converted to a (R,R)-oxazolidin-2-one diastereoisomer of Formula I by treatment with a base such as triethylamine, pyridine, 2,6-lutidine, 2,4,6-collidine, N-methylmorpholine, and the like, alone or in combination with sodium hydride, and the source of carbonyl groups such as phosgene then is added. Under these conditions, the $R^4$ protecting group is removed and cyclization to the oxazolidin-2-one ring occurs directly. The desired intermediate of Formula I then is isolated and purified as previously described.

The starting materials of Formula II can be readily prepared by reductive amination of the (R)-chiral form of an amine of the formula:

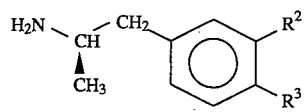

with an aldehyde $R^4CH=O$, in which $R^2$, $R^3$, and $R^4$ are as previously defined, under conditions which remove water so as to form an imine, followed by hydrogenation such as with Raney nickel to form a compound of the formula:

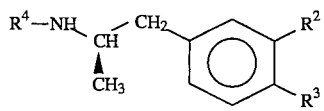

Under these conditions, the chirality of the carbon atom adjacent to the amino group is maintained in the compound of Formula VI. The compound of Formula VI then is allowed to react with a compound of the formula:

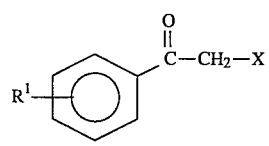

in which $R^1$ is as previously defined and X is a leaving group as for example a reactive halogen such as bromo or chloro, tosyl, mesyl, to yield the starting material of Formula II.

The following examples will serve to further typify the process but should not be construed as limiting the scope thereof which is defined solely by the appended claims.

EXAMPLE 1

A solution of 5 g. of (R)-N-(3,4-dimethoxybenzyl)-N-(3-chlorophenylcarboxymethyl)-1-(3,4-dimethoxyphenyl)-prop-2-ylamine hydrochloride in 100 mL of methanol at −78° C. is treated with 0.71 g. of sodium borohydride, added in several portions over one hour. The mixture is stirred for an additional hour and then allowed to reach room temperature. The solvent is removed by evaporation to yield (R)-N-(3,4-dimethoxybenzyl)-N-[2-(3-chlorophenyl)-2-hydroxyeth-1-yl]-1-(3,4-dimethoxyphenyl)-prop-2-ylamine, which is dissolved in methylene chloride, washed with 3N aqueous sodium hydroxide and brine, and dried over magnesium sulfate. $^1$H NMR (250 MHz, CDCl$_3$) d 1.02 (d, 3H, J=6.3 Hz), 2.4–2.7 (m, 4H), 3.1–3.25 (m, 1H), 3.35 (½ABq, 1H, J=13.3 Hz), 3.69 (s, 3H), 3.75 (s, 3H), 3.81 (br. s, 6H), 3.7–3.8 (m, 1H), 4.21 (m, minor isomer C<u>H</u>OH), 4.55 (m, major isomer C<u>H</u>OH), 6.52–6.76 (m, 6H), 7.19–7.33 (m, 4H). The product contains 97.9% R,R diastereoisomer and 2.1% S,R diastereoisomer.

EXAMPLE 2

(R)-N-(3-methoxy-4-n-butoxybenzyl)-N-(3-chlorophenylcarboxymethyl)-1-(3,4-dimethoxyphenyl)-prop-2-ylamine hydrochloride is subjected to the same procedure as described in Example 1 to yield 97.1% R,R and 2.9% S,R diastereoisomeric (R)-N-(3-methoxy-4-n-butoxybenzyl)-N-[2-(3-chlorophenyl)-2-hydroxyeth-1-yl]-1-(3,4-dimethoxyphenyl)-prop-2-ylamine. $^1$H NMR (250 MHz, CDCl$_3$) δ0.98 (t, 3H, J=7.3 Hz), 1.04 (d, 3H, J=6.5 Hz), 1.5 (m, 2H), 1.83 (m, 2H), 2.4–2.8 (m, 4H), 3.2 (m, 1H), 3.40 (½ABq, 1H, J$_{AB}$=13.3 Hz), 3.7–3.8 (m, 1H), 3.71 (s, 3H), 3.78 (s, 3H), 3.85 (s, 3H), 4.00 (t, 2H, J=6.7 Hz), 4.27 (m, minor isomer C<u>H</u>OH), 4.57 (m, major isomer C<u>H</u>OH), 6.57–6.78 (m, 6H), 7.15–7.32 (m, 4H).

EXAMPLE 3

Use of the correspondingly N-protected (R)-N-(3-chlorophenylcarboxymethyl)-1-(3,4-dimethoxyphenyl)-prop-2-ylamine salts in the procedure of Example 1 yields the following compounds with the indicated diastereoisomeric enrichment: (R)-N-(2-methoxybenzyl)-N-[2-(3-chlorophenyl)-2-hydroxyeth-1-yl]-1-(3,4-dimethoxyphenyl)-prop-2-ylamine, de 64.8%; (R)-N-(3-methoxybenzyl)-N-[2-(3-chlorophenyl)-2-hydroxyeth-1-yl]-1-(3,4-dimethoxyphenyl)-prop-2-ylamine, de 91%; (R)-N-(4-methoxybenzyl)-N-[2-(3-chlorophenyl)-2-hydroxyeth-1-yl]-1-(3,4-dimethoxyphenyl)-prop-2-ylamine, de 87.2%; (R)-N-(3,4-dimethoxybenzyl)-N-[2-(3-chlorophenyl)-2-hydroxyeth-1-yl]-1-(3,4-dimethoxyphenyl)-prop-2-ylamine, de 96.0%; (R)-N-(3,4-diethoxybenzyl)-N-[2-(3-chlorophenyl)-2-hydroxyeth-1-yl]-1-(3,4-dimethoxyphenyl)-prop-2-ylamine, de 94.6%; (R)-N-(3-methoxy-4-n-butoxybenzyl)-N-[2-(3-chlorophenyl)-2-hydroxyeth-1-yl]-1-(3,4-dimethoxyphenyl)-prop-2-ylamine, de 95.2%; (R)-N-(4-t-butoxybenzyl)-N-[2-(3-chlorophenyl)-2-hydroxyeth-1-yl]-1-(3,4-dimethoxyphenyl)-prop-2-ylamine, de 86.0%; (R)-N-(3-methoxy-4-n-heptoxybenzyl)-N-[2-(3-chlorophenyl)-2-hydroxyeth-1-yl]-1-(3,4-dimethoxyphenyl)-prop-2-ylamine, de 93.1%; (R)-N-(3-methoxy-4-benzyloxybenzyl)-N-[2-(3-chlorophenyl)-2-hydroxyeth-1-yl]-1-(3,4-dimethoxyphenyl)-prop-2-ylamine, de 93.3%; (R)-N-(3,4-dichlorobenzyl)-N-[2-(3-chlorophenyl)-2-hydroxyeth-1-yl]-1-(3,4-dimethoxyphenyl)-prop-2-ylamine, de 87.2%; (R)-N-(3,4-methylenedioxybenzyl)-N-[2-(3-chlorophenyl)-2-hydroxyeth-1-yl]-1-(3,4-dimethoxyphenyl)-prop-2-ylamine, de 96.0%; (R)-N-(3,4,5-trimethoxybenzyl)-N-[2-(3-chlorophenyl)-2-hydroxyeth-1-yl]-1-(3,4-dimethoxyphenyl)-prop-2-ylamine, de 96.0%; and (R)-N-(β-naphthylmethyl)-N-[2-(3-chlorophenyl)-2-hydroxyeth-1-yl]-1-(3,4-dimethoxyphenyl)-prop-2-ylamine, de 87.6%.

EXAMPLE 4

By conducting the reduction of Example 1 at different temperatures, the following ratios of R,R to S,R are obtained as measured by HPLC:

| Temp. | % R, R | % S, R |
|---|---|---|
| 25° C. | 82.0 | 18.0 |
| 0° C. | 88.0 | 12.0 |
| −10° C. | 89.8 | 10.2 |
| −20° C. | 90.5 | 9.5 |
| −40° C. | 91.8 | 8.2 |
| −60° C. | 94.2 | 5.8 |
| −78° C. | 95.9 | 4.1 |

EXAMPLE 5

A solution of 0.8 g. of (R)-N-(3,4-dimethoxybenzyl)-N-[2-(3-chlorophenyl)-2-hydroxyeth-1-yl]-1-(3,4-dimethoxyphenyl)-prop-2-ylamine in 10 mL of toluene is added to a slurry of 64 mg. of sodium hydride (60% oil slurry) in 5 mL of toluene at room temperature. The reaction mixture is stirred for one hour, 0.11 mL of triethylamine is added, and the reaction mixture is stirred for an additional 30 minutes. A 1.93M solution of phosgene (0.9 mL) is added and the reaction mixture is stirred for one hour and quenched with 10% hydrochloric acid. Additional toluene is added and the mixture is sequentially washed with dilute hydrochloric acid, 3N sodium hydroxide, and brine, after which it is dried over magnesium sulfate and concentrated to yield (R,R)-3-[1-(3,4-dimethoxyphenyl)prop-2-yl]-5-(3-chlorophenyl)oxazolidin-2-one which is further purified by recrystallization from 1:7 ethanol:heptane to yield white crystals. Gas chromatography indicates the chemical purity is 99.9% and HPLC indicates the optical purity is 99.6%. $^1$H NMR (250 MHz, CDCl$_3$) d 1.26 (d, 3H, J=6.7 Hz), 2.65–2.85 (m, 2H), 3.25 (m, 1H), 3.8–3.9 (m, 1H), 3.82 (s, 3H), 3.86 (s, 3H), 4.34 (m, 1H), 5.35 (m, 1H), 6.6–7.4 (m, 7H).

EXAMPLE 6

The starting material used in Example 1 can be obtained by refluxing 5 g. of (R)-1-(3,4-dimethoxyphenyl)-prop-2-ylamine and 5.11 g. of 3,4-dimethoxybenzaldehyde in 100 mL of toluene in a Dean-Stark apparatus until the formation of water ceases (about 10 to 15 hours). The crude imine (about 10 g.) is isolated by evaporation of the toluene and hydrogenated with 10 g. of Raney nickel in 100 mL of ethanol at 50 psi and 25° C. for 3 hours.

The catalyst is removed by filtration and the solvent removed from the filtrate by evaporation. The volatiles are removed on a Kugelrohr apparatus to yield (R)-N-(3,4-dimethoxybenzyl)-1-(3,4-dimethoxyphenyl)-prop-2-ylamine. $^1$H NMR (250 MHz, CDCl$_3$) d 1.11 (d, 3H, J=6.2 Hz), 2.64 (d, 2H, J=6.7 Hz), 2.8–3.0 (m, 1H), 3.64 and 3.79 (ABq, 2H, J$_{AB}$=13.1 Hz), 3.82 (s, 3H), 3.83 (s, 3H), 3.85 (br. s, 6H), 6.67–6.80 (m, 6H).

A mixture of 5.3 g. of (R)-N-(3,4-dimethoxybenzyl)-1-(3,4-dimethoxyphenyl)-prop-2-ylamine, 3.94 g. of 3-chlorophenylcarboxymethyl bromide, and 4.9 g. of sodium carbonate in 50 mL of methylene chloride and 20 mL of water is stirred at room temperature for 16 hours. Upon completion of the reaction as determined by TLC and HPLC, the reaction mixture is diluted with methylene chloride, the aqueous layer is separated, and the organic layer is washed twice with 10% aqueous hydrochloric acid, dried over magnesium sulfate, and concentrated to yield (R)-N-(3,4-dimethoxybenzyl)-N-(3-chlorophenylcarboxymethyl)-1-(3, 4-dimethoxyphenyl)-prop-2-ylamine hydrochloride.

EXAMPLE 7

A solution of 5.0 g. of (R)-N-(3-methoxy-4-n-butoxybenzyl)-N-[2-(3-chlorophenyl)-2 -hydroxyeth-1-yl]-1-(3,4-dimethoxyphenyl)-prop-2-ylamine (obtained in Example 2) in 45 mL of toluene is added to 406 mg. of sodium hydride at room temperature. The mixture is stirred for one hour, 1.29 mL of 2,6-lutidine are added, and stirring is continued for 30 minutes. The reaction mixture then is added with stirring to 5.74 mL of a 20% solution of phosgene in toluene which has been cooled to 0° C. Excess phosgene is destroyed with 3N sodium hydroxide and the reaction mixture diluted with toluene, washed sequentially with 3N sodium hydroxide and brine, dried over magnesium sulfate, and evaporated to yield (R,R)-3-[1-(3,4-dimethoxyphenyl-)prop-2-yl]-5-(3 -chlorophenyl)oxazolidin-2-one. This is further purified by stirring in heptane at 55° C. for 15 minutes, filtering, washing with additional heptane, and recrystallization from 5:4 ethyl acetate:heptane to yield white crystals. Gas chromatography indicates the chemical purity is 99.3% and HPLC indicates the de is 99.6%.

$^1$H NMR (250 MHz, CDCl$_3$) δ1.26 (d, 3H, J=6.7 Hz), 2.65–2.85 (m, 2H), 3.25 (m, 1H), 3.8–3.9 (m, 1H), 3.82 (s, 3H), 3.86 (s, 3H), 4.34 (m, 1H), 5.35 (m, 1H), 6.6–7.4 (m, 7H).

EXAMPLE 8

A mixture of 54.8 g. of 1-bromobutane, 30.0 g. of 3-methoxy-4-hydroxybenzaldehyde, and 41.5 g. of potassium carbonate in 200 mL of dimethylformamide is stirred at room temperature for 16 hours. Three hundred milliliters of ethyl acetate are added and the reaction mixture is washed sequentially with 3N hydrochloric acid (twice), 3N sodium hydroxide, and brine. The solution is dried over magnesium sulfate and concentrated by evaporation to yield 40 g. of 3-methoxy-4-n-butoxybenzaldehyde. $^1$H NMR (250 MHz, CDCl$_3$) δ 0.99 (t, 3H, J=7.3 Hz), 1.45–1.6 (m, 2H), 1.85–1.95 (m, 2H), 3.92 (s, 3H), 4.11 (t, 2H, J=6.7 Hz), 6.97 (m, 1H), 7.43 (m, 2H), 9.84 (s, 1H).

A mixture of 40.1 g. of 3-methoxy-4-n-butoxybenzaldehyde and 35.88 g. of (R)-1-(3,4-dimethoxyphenyl)prop-2-ylamine in 184 mL of n-butanol is heated at reflux for 2 hours. Approximately 50% of the n-butanol is removed by distillation and 92 mL of fresh n-butanol are added. After removal of an additional 50% of n-butanol, the solution of 3-methoxy-4-n-butoxy-1-(1-[3,4-dimethoxyphenyl]prop-2-yl-iminomethyl)benzene is combined with 0.1 eq. (140 mg. wet weight) of Raney nickel and subjected to hydrogenation at 100° C. and 50 psi. After 8 hours the reaction mixture was cooled, the catalyst removed by filtration, and the solvent removed by evaporation to yield R-N-(3-methoxy-4-n-butoxybenzyl)-1-(3,4-dimethoxyphenyl)prop-2-ylamine. $^1$H NMR (250 MHz, CDCl$_3$), δ0.97 (t, 3H, J=7.3 Hz), 1.11 (d, 3H, J=6.1 Hz), 1.5 (m, 2H), 1.8 (m, 2H), 2.63 (m, 2H), 2.9 (M, 1H), 3.64 and 3.8 (ABq, 2H, J$_{AB}$=13.0 Hz), 3.80 (s, 3H), 3.83 (s, 3H), 3.85 (s, 3H), 3.99 (t, 2H, J=6.7 Hz), 6.67–6.8 (m, 6H).

A mixture of 1.5 g. of (R)-N-(3-methoxy-4-n-butoxybenzyl)-1-(3,4-dimethoxyphenyl)prop-2-ylamine, 906 mg. of 3-chlorophenylcarboxymethyl bromide, and 401 mg. of potassium carbonate in 15 mL of dimethylformamide is stirred at room temperature. When the reaction is substantially complete as indicated by TLC, 40 mL of toluene and 100 mL of water are added. The aqueous layer is separated and extracted with 25 mL of toluene. The combined toluene extracts and original organic layer are washed with water and concentrated by evaporation. Thirty milliliters of methanol containing 1.3 mL of 3N hydrochloric acid are added and the solvents are evaporated. The residue is dried in vacuo to yield 2.2 g. (98.7%) of (R)-N-(3-methoxy-4-n-butoxybenzyl)-N-(3-chlorophenylcarboxymethyl)-1-(3,4 -dimethoxyphenyl)prop-2-ylamine hydrochloride.

What is claimed is:

1. A process for the preparation of an (R,R)-oxazolidin-2-one diastereoisomer of the formula:

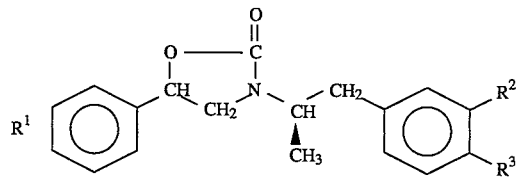

wherein

R$^1$ is hydrogen, halogeno, alkyl, alkoxy or trifluoromethyl, and

R$^2$ is hydrogen, lower alkyl, carbo(lower alkoxy), or lower alkoxy group; and

R$^3$ is hydrogen, lower alkyl, carbo(lower alkoxy), or lower alkoxy group, substantially free of the corresponding (S,R)-oxazolidin-2-one diastereoisomer comprising the steps of:

(i) reducing an acid addition salt of a ketone of the formula:

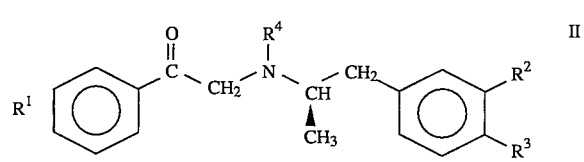

wherein each of R$^1$, R$^2$, and R$^3$ is as defined above and R$^4$ is an amino protecting group, to form a secondary alcohol of the formula:

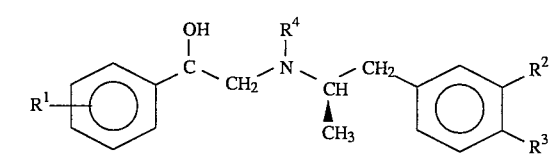

wherein the secondary alcohol is of predominantly one chiral form in preference to the other;

(ii) removing the R$^4$ amino protecting group to form a secondary amine of the formula:

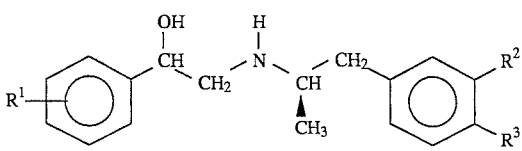

wherein each of $R^1$, $R^2$, and $R^3$ is as defined above, and (iii) allowing said secondary amine to react with a carbonic acid derivative to preferentially form said (R,R)-oxazolidin-2-one.

2. The process according to claim 1 wherein said acid addition salt of said ketone is reduced at temperatures of from about 0° C. to about −78° C.

3. The process according to claim 2 wherein carbonic acid derivative is carbonyl diimidazole.

4. The process according to claim 1 wherein the removal of said amino protecting group from said secondary alcohol to form a secondary amine is conducted in the same step as said secondary amine is allowed to react with said carbonic acid derivative.

5. The process according to claim 4 wherein said secondary alcohol is allowed to react with an heterocyclic amine base and phosgene to said (R,R)-oxazolidin-2-one.

6. The process according to claim 1 including the step of isolating said (R,R)-oxazolidin-2-one diastereoisomer substantially free of the corresponding (S,R)-diastereoisomer.

7. The process according to claim 1 wherein each of $R^2$, and $R^3$ is alkoxy of 1 to 6 carbon atoms.

8. The process according to claim 7 wherein each of $R^2$, and $R^3$ is methoxy.

9. The process according to claim 1 wherein each of $R^2$, and $R^3$ is alkylidene of 1 to 6 carbon atoms.

10. The process according to claim 9 wherein each of $R^2$, and $R^3$ is isopropylidene.

11. The process according to claim 1 wherein $R^1$ is chloro.

12. The process according to claim 11 wherein $R^1$ is m-chloro.

13. The process according to claim 1 wherein $R^4$ is an unsubstituted or substituted benzyl group having alkoxy, halogeno, or aryl substituents.

14. The process according to claim 1 wherein $R^4$ is 2-methoxybenzyl, 3-methoxybenzyl, 4-methoxybenzyl, 3,4-dimethoxybenzyl, 3,4-diethoxybenzyl, 3-methoxy-4-n-butoxybenzyl, 3-methoxy-4-n-heptoxybenzyl, 3-methoxy-4-benzyloxybenzyl, 3,4-dichlorobenzyl, 3,4-methylenedioxybenzyl, 3,4,5-trimethoxybenzyl, or β-naphthylmethyl.

15. The process according to claim 14 wherein $R^4$ is 3,4-dimethoxybenzyl.

16. The process according to claim 14 wherein $R^4$ is 3-methoxy-4-n-butoxybenzyl.

17. A process for the preparation of (R,R)-3-[1-(3,4-dimethoxyphenyl)prop-2-yl]-5-(3-chlorophenyl)oxazolidin-2-one substantially free of the (S,R)-3-[1-(3,4-dimethoxyphenyl)prop-2-yl]-5-(3-chlorophenyl)oxazolidin-2-one diastereoisomer comprising the steps of:

(i) reducing an acid addition salt of an N-protected N-(3-chlorophenylcarboxymethyl)-1-(3,4-dimethoxyphenyl)prop-2-ylamine to form the correspondingly N-protected N-[2-(3-chlorophenyl)-2-hydroxyeth-1-yl]-1-(3,4-dimethoxyphenyl)-prop-2-ylamine of predominantly one chiral form in preference to the other chiral form;

(ii) removing the amino protecting group from said N-protected N-[2-(3-chlorophenyl)-2-hydroxyeth-1-yl]-1-(3,4-dimethoxyphenyl)-prop-2-ylamine; and (iii) allowing the resultant N-[2-(3-chlorophenyl)-2-hydroxyeth-1-yl]-1-(3,4-dimethoxyphenyl)-prop-2-ylamine to react with carbonyl diimidazole to preferentially form said (R,R)-3-[1-(3,4-dimethoxyphenyl)prop-2-yl]-5-(3-chlorophenyl)oxazolidin-2-one.

18. The process according to claim 17 wherein said amino protecting group is removed simultaneously from said N-protected N-[2-(3-chlorophenyl)-2-hydroxyeth-1-yl]-1-(3,4-dimethoxy-phenyl)-prop-2-ylamine wherein said N-protected N-[2-(3-chlorophenyl)-2-hydroxyeth-1-yl]-1-(3,4-dimethoxyphenyl)-prop-2-ylamine is allowed to react with phosgene to preferentially form said (R,R)-3-[1-(3,4-dimethoxy-phenyl)prop-2-yl]-5-(3-chlorophenyl)oxazolidin-2-one.

19. The process according to claim 17 wherein said N-protecting group is an unsubstituted or substituted benzyl group having alkoxy, halogeno, or aryl substituents.

20. The process according to claim 19 wherein said N-protecting group is 3,4-dimethoxy benzyl.

21. The process according to claim 20 wherein said N-protecting group is 3-methoxy-4-butoxybenzyl.

\* \* \* \* \*